United States Patent [19]

Gowan, Jr.

[11] Patent Number: 5,141,672

[45] Date of Patent: Aug. 25, 1992

[54] QUATERNARY AMMONIUM FLUORESCENT WHITENING AGENT, PRODUCTS THEREOF

[75] Inventor: John W. Gowan, Jr., Washington, D.C.

[73] Assignee: Westvaco Corporation, New York, N.Y.

[21] Appl. No.: 462,231

[22] Filed: Jan. 9, 1990

[51] Int. Cl.$^5$ .................. C09K 11/06; C07C 229/38
[52] U.S. Cl. ................. 252/301.21; 560/45; 562/452
[58] Field of Search ............. 252/301.21; 560/45; 562/452

[56] References Cited

U.S. PATENT DOCUMENTS

| | | | |
|---|---|---|---|
| 3,966,573 | 6/1976 | Bean | 560/45 |
| 3,968,085 | 7/1976 | Rabilloud et al. | 260/75 N |
| 4,260,816 | 4/1981 | Albright et al. | 560/45 |
| 4,350,822 | 9/1982 | Albright et al. | 560/45 |
| 4,481,186 | 11/1984 | Deckner | 424/59 |
| 4,501,767 | 2/1985 | Iimure | 427/44 |
| 4,539,385 | 9/1985 | Geist et al. | 528/100 |
| 4,607,073 | 8/1986 | Sakashita et al. | 524/404 |
| 4,642,322 | 2/1987 | Wehner et al. | 524/191 |
| 4,696,999 | 9/1987 | Spies et al. | 528/319 |

FOREIGN PATENT DOCUMENTS

| | | | |
|---|---|---|---|
| 0109454 | 6/1983 | Japan | 562/452 |
| 0608798 | 5/1978 | U.S.S.R. | 562/452 |
| 128912 | 6/1919 | United Kingdom | 560/45 |
| 788100 | 12/1957 | United Kingdom | 560/45 |

OTHER PUBLICATIONS

Occupational Health in the Chemical Industry, pp. 497–506, Medichem Calgary 1983 Association, Calgary (1983).

Primary Examiner—Margaret Medley

[57] ABSTRACT

A cationic group-carrying fluorescent compound of the formula

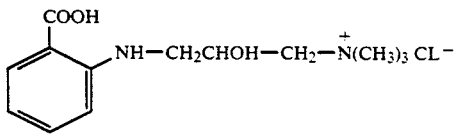

wherein
R is H, $(C_1-C_6)$alkyl, $(C_2-C_6)$alkenyl, $(C_2-C_6)$-alkynyl or $(C_2-C_6)$alkoxyl;
R' is $(C_1-C_{16})$alkylamine, $(C_2-C_{16})$alkenylamine, $(C_2-C_{16})$alkynylamine or $(C_1-C_{16})$ quaternary ammonium salts thereof, which may further comprise O, N, S or halogen;
R" is H or $-NH-(R')^+ X^-$; and
$X^-$ is an anion.

A fluorescent agent comprises the above compound and a whitening composition comprises a whitening amount of the compound and a filler or binder.

3 Claims, No Drawings

QUATERNARY AMMONIUM FLUORESCENT WHITENING AGENT, PRODUCTS THEREOF

BACKGROUND OF INVENTION

This invention is related to co-pending U.S. application Ser. No. 07/347,260, filed on May 4, 1989 now U.S. Pat. No. 5,026,507, entitled "Fluorescent Whitening Agents, Products Comprising the Agent and Method of Use Thereof", U.S. application Ser. No. 07/347,328, filed on May 4, 1989 now U.S. Pat. No. 4,954,566, entitled "Preparation of Polymers with Pendant Organic Moieties Bound thereto via Ester and/or Amide Bridges", U.S. application Ser. No. 07/426,866 filed on Oct. 26, 1989 now abandoned, entitled "Cellulosic Pulp of High Brightness and Retention Characteristics and Methods of Preparation Thereof", U.S. application Ser. No. 07/401,624 filed on Aug. 31, 1989 now U.S. Pat. No. 4,963,625, entitled "Polyacrylamide Whitener of High Brightness and Retention and Low Toxicity and Method of Increasing Paper Whiteness" and U.S. application Ser. No. 07/401,427 filed on Aug. 31, 1989 now U.S. Pat. No. 5,043,370, entitled "Polyalkylene Imide of High Brightness and Retention Characteristics and Low Toxicity and Method of Increasing Paper Whiteness", all by the present inventors and assignors.

This invention relates to quaternary ammonium fluorescent compounds, products comprising them, a method for preparing the compounds, and to their use as whitening agents, particularly in coating formulations to increase the whiteness of paper products. The present agents evidence low biological toxicity as well as high whitening characteristics and are therefore particularly suited for packaging food products.

The brightness of bleached paper products can be increased by adding fillers such as titanium dioxide and fluorescent whitening agents to the paper or coating the paper with such products However, the use of fluorescent whitening agents is usually more economical, and is therefore progressively becoming more common than the use of titanium dioxide.

On the other hand, the use of known fluorescent whitening agents is not free from biological and environmental consequences. This becomes of particular importance when applied to the manufacture of paper products which are to be placed in contact with edibles such as foods and the like.

At the present time there are no known fluorescent whitening agents of low biological and environmental impact which are being used in the manufacture of paper products in the food industry in the United States.

Only one fluorescent whitening agent has, to the present time, been approved by the Food and Drug Administration (FDA) for use in food related applications. This agent is manufactured by Ciba-Geigy and sold as Uvitex OB. The product is highly insoluble in water and is marketed as a plastic additive (U.S. Pat. No. 4,642,322 to Wehner et al).

Anthranilic acid and various derivatives thereof have been known, as are known their low toxicity and high fluorescent characteristics.

U.S. Pat. No. 4,642,322 referred to above discloses the addition of anthranilic acid amide as a stabilizer to thermoplastics. Titanium dioxide is also utilized by this patent. However, the product is provided not as a coating formulation for use in paper products but as a thermoplastic for use in plastics.

Amino benzoic acids have been disclosed as being useful for the preparation of polybenzamide in the presence of U.S. Pat. No. 4,696,999 discloses such products as well as amino benzoic acid esters for use in the synthesis of polybenzamides. The amino benzoic acids and esters thereof described in this patent are, however, meta- and para-amino compounds, and are therefore positional isomers of the esters and acids of this invention. In addition, this patent proposes the use of these compounds to form pulps of short fiber materials with high stability values. This patent also discloses in Example A a condensation reaction of 4-aminobenzoic acids with titanium chloride but nowhere is there a disclosure of use of the compounds in paper products.

U.S. Pat. No. 4,481,186 to Speakman describes a copolymer pigment dispersant suitable for use in the preparation of paints and para-aminobenzoic acid is one of the components utilized. Another component is titanium dioxide which is used as a pigment for color. No mention of any utility in terms of the utilization of the products for coating paper is stated.

Aminobenzoic acid is also used in admixture with a coloring agent such as titanium dioxide for the preparation of cosmetic and skin treatment compositions in U.S. Pat. No. 4,481,186. The prior art cosmetic and skin treatment compositions are generally speaking coating formulations but they are not paper whitening coating compositions.

A condensate of para- or meta-aminobenzoic acid and titanium dioxide is disclosed in U.S. Pat. No. 4,607,703. These materials are incorporated into molding polyamide compositions but are not suggested for use in paper coatings.

Titanium dioxide is used as a pigment and 4-aminobenzoic acid as a compound capable of providing an activated ester group in the preparation of self cross-linking heat-curable grinding resins in U.S. Pat. No. 4,539,385. No mention of paper coatings in this patent can be found.

Fluorescent whitening agents work by emitting bluish light upon excitation in the long ultra violet region (about 350–400 nm). This light can compensate for the yellowness inherent to paper products.

For example, methyl anthranilate and methyl N-methyl anthranilate have been reported to be non-mutagenic in short-term microbial assays (Shimizu, H. and Takemura, N., "Mutagenicity of Some Aniline Derivatives", in Orford, R. R., Cowell, J. W., Jamieson, G. G., and Love, E. J., editors, "Occupational Health in the Chemical Industry", pp 497–506, MEDICHEM Calgary 1983 Association, Calgary (1983).

U.S. Pat. No. 4,501,767 discloses a method of forming a multicoat by using an accelerator which can be the reaction product of an ortho-, meta- or para-amino benzoic acid with a polymerizable unsaturated carboxylic acid or polymerizable unsaturated alcohol and an epoxy resin or polyepoxy compound. This prior art patent contains no suggestion of the epoxy component being a quaternary ammonium derivatized epoxide.

U.S. Pat. No. 3,968,085 discloses aromatic polyamine compositions useful as hardening agents. The polyamines may be prepared by using an aminobenzoic acid as a reactant. The polyamines of this prior art patent are also disclosed as being hardeners for epoxy resins. This patent does not mention any reaction with an anthranilic acid or ester thereof with a quaternarized epoxy resin.

Accordingly, there is still a need for a low toxicity inexpensive whitening agent suitable as a paper additive for use in packaging in the food industry.

SUMMARY OF INVENTION

This invention relates to cationic group-carrying fluorescent compound of the formula

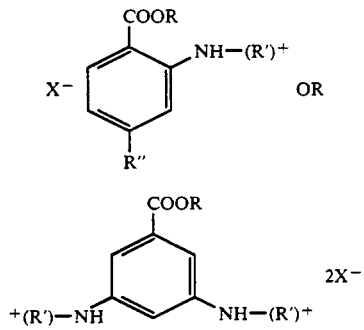

Wherein

R is H, $(C_1-C_6)$alkyl, $(C_2-C_6)$alkenyl, $(C_2-C_6)$-alkynyl or $(C_1-C_6)$alkoxyl;

R' is a $(C_1-C_{16})$alkylamine, $(C_2-C_{16})$alkenylamine, $(C_2-C_{16})$ alkynylamine or $(C_1-C_{16})$ quaternary ammonium salts thereof, which may further comprise O, N, S or halogen;

R" is H or $-NH-(R')^+X^-$; and $X^-$ is an anion.

Also part of this invention is a fluorescent agent comprising the above compound Also disclosed herein is a whitening composition, which comprises a paper whitening amount of the compound described above; and a filler.

Also disclosed herein is a paper of high whiteness and low biological toxicity which comprises a whitening amount of the composition described above.

Still part of this invention is a food product wrapped with and/or packaged in the high whiteness, low biological toxicity paper of this invention.

Also disclosed herein is a method of preparing a fluorescent whitener carrying a cationic group, which method comprises reacting a fluorescent compound having at least one amine residue with a cationic group-carrying compound capable of reacting with the amine residue of the fluorescent compound under conditions effective to bind said fluorescent compound through said amine residue and said cationic compound by other than the cationic group and obtain said fluorescent whitener with said cationic group; and separating said fluorescent whitener from the rest of the reaction mixture.

Still another aspect of this invention is a method of increasing the whiteness of a paper while preserving its low biological toxicity which comprises admixing to cellulosic ingredients a whitening amount of the compound of this invention to form said paper.

Also part of the invention described herein is a method of increasing the whiteness of a paper while preserving its low biological toxicity comprising admixing to the paper ingredients an amount of the composition described above containing a whitening amount of the fluorescent compound.

Still part of this invention is a method of increasing the whiteness of a cellulosic product comprising coating a whitening amount of the fluorescent compound of the invention onto the cellulosic product.

Also within the confines of the invention is a method of increasing the whiteness of a cellulosic product by coating thereon an amount of the whitening composition provided herein capable of delivering a whitening amount of the fluorescent compound of this invention.

A more complete appreciation of the invention and many of the attendant advantages thereof will be readily perceived as the same becomes better understood by reference to the following detailed description. Other objects, advantages and features of the present invention will thus become apparent to those skilled in the art from the following discussions.

DETAILED DESCRIPTION

This invention arose from a desire of the inventor to improve the production of paper suitable for utilization in the packaging of food products There is in general a demand for biologically safe whiteners which can be used to improve the appearance of wrapping and packaging paper utilized in the food industry However, up to the present time there has been not one biologically safe fluorescent whitener suitable for use in the production of whitening agents and/or whitened papers intended specifically for use in this filed. This invention provides an agent of high whiteness and low biological toxicity which is suitable for use in paper wrappings intended for use with food products.

The cationic group-carrying fluorescent compound of the invention has the formula

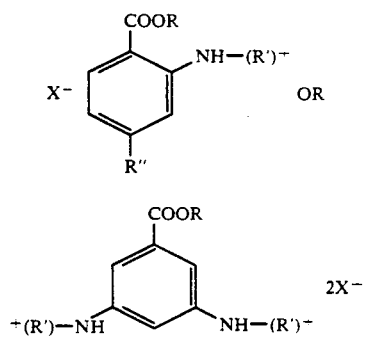

Wherein

R is H, $(C_1-C_6)$alkyl $(C_2-C_6)$alkenyl, $(C_2-C_6)$-alkynyl or $(C_1-C_6)$alkoxyl;

R' is a $(C_1-C_{16})$alkylamine, $(C_2-C_{16})$alkenylamine, $(C_2-C_{16})$alkynylamine, or $(C_1-C_{16})$alkylamine quaternary ammonium salts thereof, which may further comprise O, N, S or halogen;

R" is H or $-NH-(R')^+X^-$; and $X^-$ is an anion.

Preferred is the compound wherein R is H. Still other preferred compounds are those wherein R' is $(C_1-C_6)$alkylamine, $(C_2-C_6)$alkenylamine, $(C_2-C_6)$alkynylamine or $(C_1-C_6)$alkoxylamine. Still another preferred embodiment is that wherein R' is $(C_1-C_6)$alkyl quaternary ammonium. All the substituents may further comprise O, N, S or halogen.

A particularly preferred embodiment of the invention is that wherein the compound is

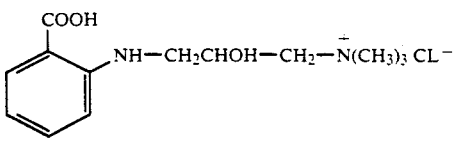

In another particularly preferred embodiment herein the invention provides a fluorescent agent comprising the compound described above. In this agent, the compound of the invention is present in an amount of about 0.001 wt. % to 99.999 wt. %, and more preferably about 10 wt. % and 90 wt. %.

Also part of the invention is a whitening composition which comprises a whitening amount of the compound of this invention, and optionally other whiteners, binders and/or known additives in amounts known in the art. Preferred amounts of the compound are about 0.01 wt. % to 99.99 wt. %, and more preferred about 10 wt. % to 90 wt. %.

In a particular embodiment the invention comprises a paper comprising a whitening amount of the compound of the invention. Preferred amounts of the fluorescent compound of the invention added to the paper are about 0.01 to 1 wt. % of the composition However, other amounts are possible as well.

Binders and other additives suitable for use with the present whitening compounds are known in the art.

Whiteners other than the present ones which may be incorporated in the composition are also known in the art. Particularly suitable is titanium dioxide When this whitener is added to the whitening composition of this invention a higher whiteness and/or brightness is attained. As an alternative to the above, the titanium dioxide whitener may also be added to the paper pulp while the present whitener is added thereto separately and/or to the finished paper product. The thus prepared paper product may then be subjected to a printing process, if desired.

Also provided herein is a food product packaged in the high whiteness, low biological toxicity paper of this invention.

When the whitening composition of the invention contains other whitening components in addition to the present whiteners, the whiteners of the invention are contained in the composition in an at least whitening amount thereof. This amount may be lower than if the composition does not comprise other whitening agents. Alternatively the presence of other whiteners may increase the whiteness of the paper products.

Various types of papers may be utilized for practicing this invention. Particularly useful papers are those made of cellulose and derivatives thereof, mixtures of cellulose and synthetic polymers and the like. However, other types of papers may also be utilized within the confines of this invention.

The whitened papers produced in accordance with this invention may be utilized for packaging almost any sort of food product By means of example it may be mentioned both dry and moist food products.

Also provided by this invention is a method of preparing a fluorescent whitener carrying a cationic group, which comprises reacting a fluorescent compound having at least one amine residue with a cationic group-carrying compound capable of reacting with the amine residue of the fluorescent compound under conditions effective to bind said fluorescent compound through said amine residue and said cationic compound through a group other than said cationic group to obtain said fluorescent whitener carrying said cationic group, and separating said fluorescent whitener from the rest of the reaction mixture.

The cationic group-carrying compound in general contains a reactive group through which it binds to the fluorescent compound.

In a preferred embodiment of the invention the cationic group-carrying compound is a cationic group-carrying epoxide. In still another embodiment the cationic group carried by the compound is a quaternary ammonium group, and more preferably the quaternary ammonium group is selected from the group consisting of $(C_2-C_8)$alkyl, $(C_2-C_8)$alkenyl, and $(C_2-C_8)$alkynyl ammonium groups.

In still another preferred embodiment of the method the fluorescent compound is selected from the group consisting of $(C_2-C_{20})$alkylamines, $(C_2-C_{20})$ alkenylamines, $(C_2-C_{20})$ alkynlamines, $(C_7-C_{30})$ arylamines, $(C_8-C_{50})$ alkyl-arylamines, $(C_8-C_{50})$alkenylarylamines, $(C_8-C_{50})$alkynyl-arylamines and derivatives thereof further comprising O, N, S or halogen and mixtures thereof.

In still another preferred embodiment the fluorescent compound is an aryl amine further comprising a carboxylic acid or carboxylic acid ester residue Still more preferred is a fluorescent compound which comprises anthranilic acid, anthranilic acid ester or a mixture thereof.

The reaction of the above method is preferably conducted at a temperature of about 50° to 150° C. and more preferably 75° to 110° C. Still more preferably the reaction is conducted in the presence of a solvent. More preferably the solvent is toluene, benzene, or xylene. However, other solvents may also be utilized as long as they do not interfere with the stability of the reactants or the products.

The fluorescent compound and the cationic group-carrying compound are typically reacted in molar equivalent amounts of about 10:1 to 1:1, and preferably about 7:1 to 5:1. When a solvent is present, the fluorescent compound, the cationic group-carrying compound and the solvent are added in amounts of about 10:1:10 to 10:1:10 being molar equivalents: molar equivalents: liters, and more preferably about 5:1:10.

In a preferred embodiment of the method described above the separation step is conducted by solvent extraction. Typically, if the reaction step is conducted in the presence of a solvent, the separation step is conducted with a different type of solvent which will extract the reactants while leaving most of the product in the reaction mixture. Typically, solvents which may be utilized for the extraction are toluene, benzene, or xylene. However, other solvents which are at least somewhat immiscible with the reaction solvent may also be utilized as long as they are capable of dissolving the chemical compounds wished extracted out from the reaction mixture.

In a typical reaction mixture the above method will provide for amounts of the fluorescent compound and the cationic group-carrying compound in a molar equivalent ratio of about 10:1 to 1:100, and more preferably about 8:1 to 1:50.

The composition of the invention may also be applied as a coating to an already formed cellulosic product. The application of the coating to the paper may be conducted by any of a number of methods generally known in the art, such as spraying, scraping, roll coating, dipping and the like Other methods may also be utilized within the confines of this invention.

Also provided herein is a method of increasing the whiteness of a paper while preserving its low biological toxicity which comprises admixing to cellulosic ingredients a whitening amount of a compound of the formula

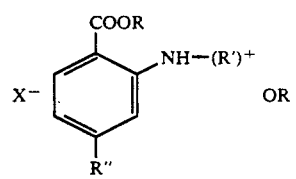

OR

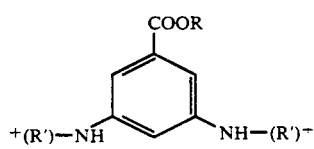

wherein

R is H, $(C_1-C_6)$alkyl, $(C_2-C_6)$alkenyl, $(C_2-C_6)$-alkynyl or $(C_1-C_6)$alkoxyl;

R' is a $(C_1-C_{16})$alkylamine, $(C_2-C_{16})$alkenylamine, $(C_2-C_{16})$alkynylamine or $(C_1-C_{16})$ quaternary ammonium salts thereof, which may further comprise O, N S or halogen;

R'' is H or $-NH-(R')^+X^-$; and $X^-$ is an anion.

The method of increasing the whiteness of a paper by admixing to the paper ingredients a whitening amount of the fluorescent compound of the invention may be conducted by various means known in the art. The fluorescent whitener of this invention may for instance be added to one ingredient and then the remaining ingredients admixed thereto Alternatively, all ingredients may be admixed to one another and then the whitener added thereto or all ingredients and the present whitener as well as other whiteners added simultaneously.

Also part of this invention is a method of increasing the whiteness of a cellulosic product while preserving its low biological toxicity which comprises admixing to the paper ingredients an amount of a composition comprising a whitening amount of the fluorescent compound of this invention, and a filler Typically, the composition is utilized in amounts delivering the amounts of fluorescent compound described above.

Also provided herein is a method for increasing the whiteness of a cellulosic product while preserving its low biological toxicity which comprises coating onto the cellulosic product a whitening amount of a compound of the formula

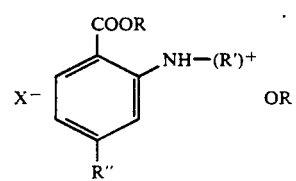

OR

-continued

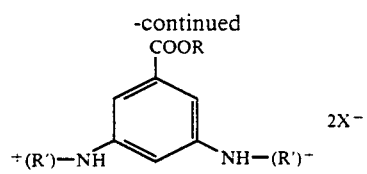

wherein

R is H, $(C_1-C_6)$alkyl, $(C_2-C_6)$alkenyl, $(C_2-C_6)$-alkynyl or $(C_1-C_6)$alkoxyl;

R' is a $(C_1-C_{16})$alkylamine, $(C_2-C_{16})$alkenylamine, $(C_2-C_{16})$alkynylamine or $(C_1-C_{16})$ quaternary ammonium salts thereof, which may further comprise O, N, S or halogen;

R'' is H or $-NH-(R')^+X^-$; and $X^-$ is an anion.

Still part of this invention is a method of increasing the whiteness of a cellulosic product while preserving its low biological toxicity which comprises coating onto the product a whitening amount of the composition described above.

Methods for coating whitening agents are known in the art and need not further be described herein For example, the agent or a composition comprising it, and optionally other ingredients may be coated by, roll coating, scraping, dipping, spraying and the like. However, other methods may also be utilized.

Having now generally described this invention, the same will be better understood by reference to certain specific examples, which are included herein for purposes of illustration only and are not intended to be limiting of the invention or any embodiment thereof, unless so specified.

EXAMPLE 1

Synthesis of Fluorescent Compound in Accordance with the Invention Starting From Anthranilic Acid

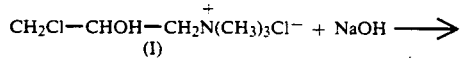

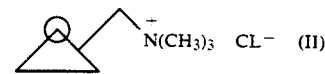

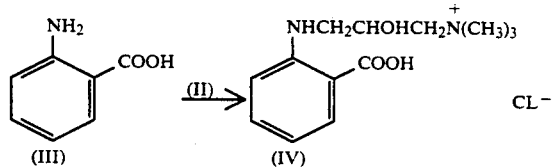

0.5 g of Compound (I) (DOW Quat 188 a product of Dow Chemical Company) were allowed to react with 10 wt. % 2N NaOH at 25° C. for 5 minutes.

To the thus resulting aqueous solution containing the epoxide (II) were added 5 g of anthranilic acid. The solution was then stirred at 47° C. for 2 hours.

Thereafter, unreacted starting materials were extracted 10 times with 25 ml of solvent.

The remaining solution containing compound(IV) was found to be highly fluorescent at 254 nm wavelength.

EXAMPLE 2

Synthesis of Fluorescent Compound in Accordance with the Invention Starting From Ethyl Anthranilate

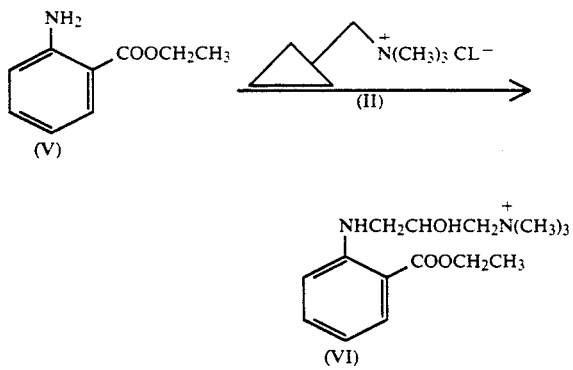

To an aqueous solution containing 0.5 g of Compound (II) prepared as described in Example 1 were added 5 g of ethylanthranilate (V). The solution was stirred at 47° C. for about 2 hours and then unreacted starting materials were extracted 10 times into 25 ml of a hydrophobic solvent.

The remaining solution containing the derivatized product (VI) is highly fluorescent at 254 nm.

EXAMPLE 3

Preparation of Solutions with Whiteners of the the Invention, Anthranilic Acid and Ethyl Anthranilate Various solutions were prepared containing the following in addition to 100 ml of water:

(1) 0.5 g of Compound (IV) (Solution 1);
(2) 0.5 g of Compound (VI);
(3) 0.5 g of Compound (III); and,
(4) 0.5 g of Compound (V).

EXAMPLE 4

Retention of Whiteners by Paper Substrate

Sheets of non-fluorescent filter paper were separately dipped in the aqueous solutions prepared as described in Example 3. The sheets were only partially dipped in the solutions and then dried and their fluorescence determined at 254 nm.

All pieces of paper filter were found to be equally fluorescent.

50 ml of water were poured over each sheet and the sheets were again dried.

The sheets dipped into solutions of compounds (IV) and (VI) evidenced the same amount of fluorescence as before being exposed to the water treatment. In addition, it was found that the fluorescence did not migrate to the portion of the sheet which was not originally dipped in the solutions.

The sheets dipped into solutions of compounds (III) and (V) showed much reduced fluorescence as well as considerable migration of the remaining fluorescence to the portions of the sheets not previously dipped in the solutions.

The invention now being fully described, it will be apparent to one of ordinary skill in the art that many changes and modifications can be made thereto without departing from the spirit or scope of the invention as set forth herein.

I claim:

1. A cationic group - carrying fluorescent compound of the formula

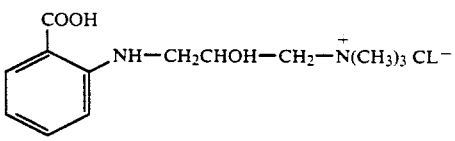

2. A whitening composition, comprising the compound of claim 1; and a filler or binder.

3. The composition of claim 2, comprising about 0.1 to 50 wt. % of the fluorescent compound.

* * * * *